United States Patent [19]
Richter

[11] 4,091,471
[45] May 30, 1978

[54] PUMP FOR AN ARTIFICIAL HEART

[75] Inventor: Christian Richter, Unterhaching, Germany

[73] Assignee: Messerschmitt-Bolkow-Blohm GmbH, Munich, Germany

[21] Appl. No.: 750,182

[22] Filed: Dec. 13, 1976

[30] Foreign Application Priority Data

Dec. 19, 1975 Germany .............................. 2557475

[51] Int. Cl.² .......................... A61F 1/24; A61M 1/03
[52] U.S. Cl. ...................................... 3/1.7; 128/1 D; 417/375; 417/394; 417/478
[58] Field of Search ............. 3/1.7; 128/1 D, DIG. 3; 417/478, 375, 392, 394

[56] References Cited

U.S. PATENT DOCUMENTS

| | | | |
|---|---|---|---|
| 3,579,644 | 5/1971 | Esmond | 3/1.7 |
| 3,814,547 | 6/1974 | Kitrilakis et al. | 417/478 X |
| 3,916,449 | 11/1975 | Davis | 3/1.7 |
| 3,919,722 | 11/1975 | Harmison | 3/1.7 |

FOREIGN PATENT DOCUMENTS

102,948   1/1938   Australia .............................. 417/394

OTHER PUBLICATIONS

"Solenoid Design for a Prosthetic Heart" by D. Freebairn et al., Transactions Amer. Soc. Artificial Internal Organs, vol. X, 1964 pp. 166–170.
"A New Type of Diaphragm Blood Pump" by A. Hawrylenko et al., Medical & Biological Engineering, vol. 5, No. 6, Nov. 1967, pp. 555–559.

*Primary Examiner*—Ronald L. Frinks
*Attorney, Agent, or Firm*—W. G. Fasse; W. W. Roberts

[57] ABSTRACT

A housing of a pump for an artificial heart comprises central, polar regions of rigid material where a rotatable connector for control and/or power supply conduits is located. An equatorial, peripheral region is made of flexible material. Connectors for inlet and outlet conduits are tangentially mounted to the equatorial region. A flat, torus shaped bellows of elastic material is positioned between two oppositely driven, spring loaded pressure plates and encloses the pump volume. An electromechanical displacement transducer provides signals proportional to the stroke of the pump. The pump may be operated by a liquid or gaseous pressure medium and its shape and structure are well adapted for implantation into a living organism, especially the human body.

16 Claims, 5 Drawing Figures

PUMP FOR AN ARTIFICIAL HEART

BACKGROUND OF THE INVENTION

The invention relates to a pump for an artificial heart, more specifically, to a device which is insertable into the blood circulatory system of a living being as an aid or substitute for a natural heart. Such devices are described, for example, in "Advances in Biomedical Engineering and Medical Physics" Volume 3, Cardiac Engineering, published by Interscience Publishers, a division of John Wiley & Sons, Inc.

Cardiac surgeons have set forth requirements for an artificial heart pump that have not been met in their entirety by the pumps presently known for this purpose. Essentially, these requirements call for a flat, rounded-off shape for a pump which is flexible throughout the largest possible area of its outer covering, and the connection conduits of which are attached in a releasable and/or swivelable manner, to the pump housing.

Furthermore, the pump shall operate smoothly, that is free of irregular shocks and it shall run as vibration-free as possible. For this purpose, gravity forces must be compensated.

The foregoing requirements pertain mainly to the application and body compatibility of the pump as such. As mentioned, these requirements have not been satisfied heretofore. However, other requirements, not relating directly to the invention, for example, requirements relating to the drive and to the pump control or to artificial heart valves to be inserted in the blood stream, have been met heretofore by a number of well known proposals.

OBJECTS OF THE INVENTION

In view of the foregoing, it is the aim of the invention to achieve the following objects, singly or in combination:

- to provide an artificial heart pump with a flat, rounded-off configuration which is flexible to as large an extent as possible within its outer covering and which has good body compatibility;
- to reduce irregular pressure changes or pressure shocks resulting from a pulsating pump output;
- to provide a pump action that operates substantially without vibrations and to compensate gravity forces;
- to provide a pump which can be easily handled during the implantation, placement, and for which the necessary connections may be easily made;
- to provide a pump which may be driven by either gaseous or liquid pressure media;
- to provide a pump having a drive system wherein sealing problems are minimized;
- to provide a pump that is as suitable for a permanent implantation as an artificial heart as it is for a time limited use, for example, in a cardiac by-pass operation;
- to provide an artificial heart pump having pressure and current flow characteristics during any work cycle which correspond substantially to those of a natural heart; and
- to provide a pump may be adjusted to different form and dimension requirements with low alteration expenditures.

SUMMARY OF THE INVENTION

According to the invention, there is provided a pump for an artificial heart having a pump housing with a shape corresponding substantially to that of a rotational ellipsoid. The housing includes central, polar regions and an equatorial region where connectors or ports for inlet and outlet conduits are tangentially mounted. The pump housing is made of rigid material in the central, polar regions and of flexible material in the equatorial region. A connector terminal, which is able to rotate at least through 90° is secured to the central region, for the connection of control and/or power supply conduits. Due to this flat, flexible shape it is easy to handle the pump during implantation and placement, and the required connections are also easily made. This flat shape also results in a good body compatibility of the pump.

Further embodiments of the invention compensate for inertia forces of moving bodies and fluids and assure the steady pulsating delivery of blood free of shocks. According to these further embodiments, a flat, torus shaped bellows made of elastic material is located between two oppositely driven pressures plates and encloses the pump volume. Inlet and outlet ports are formed as part of the bellows and extend in a tangential direction relative to the bellows. These ports penetrate or extend through the pump housing in its elastic region and are tightly sealed to the housing at the point of penetration. The pressure plates are spring loaded for the reduction of impact or shock forces by providing the pressure plates with radially extending and/or tangentially directed leaf springs which extend from the pressure plates in spaced apart fashion, for example, as fingers would from a hand. Especially where a relatively thin walled torus shaped bellows is used these springs may be bent to encircle the bellows whereby the springs of one pressure plate reach into the spaces between the "fingers" or springs of the other pressure plate and vice versa when the bellows is compressed.

According to a further feature of the invention, a rotatable connector terminal comprises a pipe or hose connection for a pressure medium conduit which supplies the drive power to the pump. The pressure medium is effective in interconnected sealed-off pressure chambers to move elastic membranes secured to rigid pressure plate drive members in opposite directions. The drive members are biased by a restoring spring force which returns the pressure plates into their starting positions. The pressure medium used may be a gas or liquid, preferably of a kind that is body compatible.

The control, for example, a closed loop control, for a drive means which itself is not part of the invention may comprise an electromechanical displacement transducer located inside the space surrounded by the torus shaped bellows. The signal conductors of the transducer lead to a connector plug on the rotatable connector terminal. In this way, through little expense, it is possible to obtain very accurate, proportional signals corresponding to the delivery or conveying efficiency of the pump, under all operating conditions. These signals may be transmitted to a suitable control arrangement for the drive means of the pump.

BRIEF FIGURE DESCRIPTION

In order that the invention may be clearly understood, it will now be described, by way of example, with reference to the accompanying drawings, wherein.

DETAILED DESCRIPTION OF PREFERRED EXAMPLE EMBODIMENTS

Figure 1:
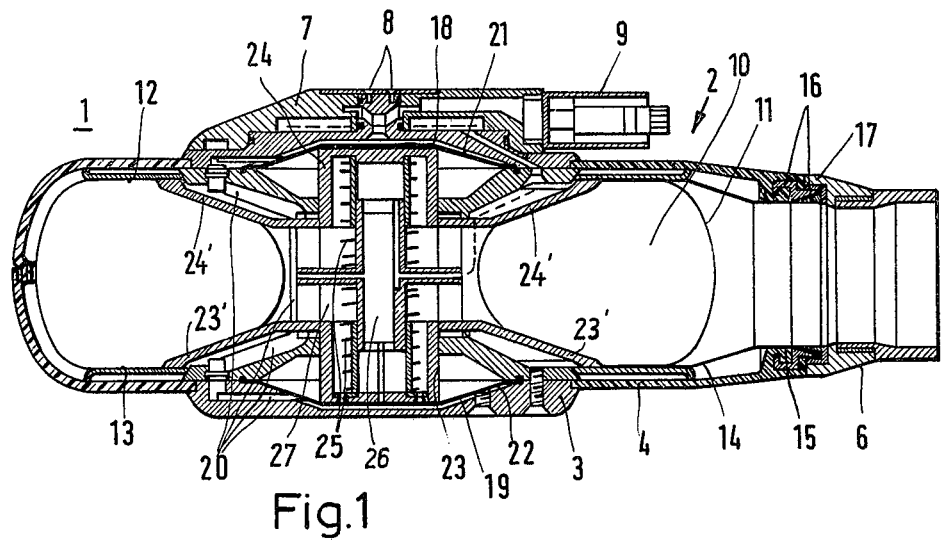
FIG. 1 is a sectional view of a pump according to the invention, for an artificial heart, wherein the section extends along line II—II in FIG. 2.
Figure 2:
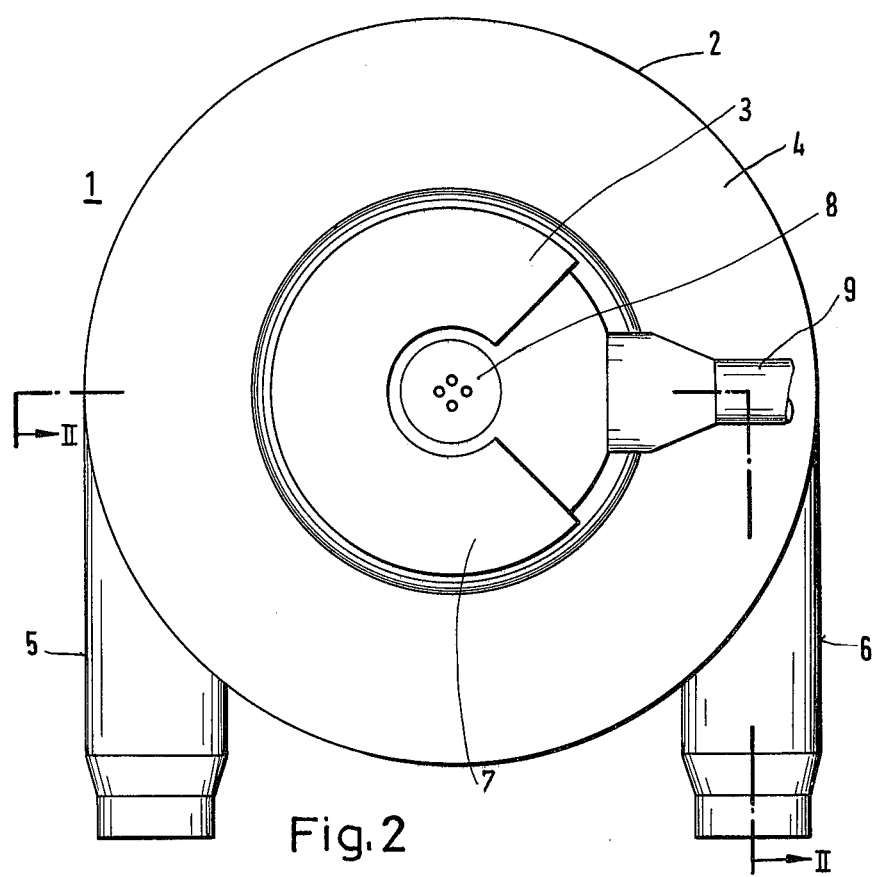
FIG. 2 is a top plan view of the pump of FIG. 1.

According to the invention, the pump 1 for an artificial heart as shown in FIGS. 1 and 2, includes a pump housing 2 comprising centrally located polar regions 3 and a peripheral, equatorial region 4. The central, polar regions are made of rigid material, for example, a body compatible metal or of synthetic material. The equatorial region 4 of said pump housing 2 is made of flexible material, e.g., synthetic material. Certain internal elements, for example 11, respectively 12, 13, of the pump, are also made of flexible material, e.g. synthetic material respectively; spring steel, as will be described below. The pump housing 2 also includes two elastically deformable inlet and outlet port means 5 and 6, mounted to the housing 2 to extend in tangential directions relative to the equatorial region 4, as shown in FIG. 2. Said port means 5 and 6 are adapted for connection to known valves such as artificial heart valves, located in respective conduits, not shown. The central region 3 of said pump housing 2 is provided with a connector means or terminal plate 7 rotatably secured to the housing means in at least one polar region. A coupling plug 8, for example, for control means, is part of the connector means. Said connector terminal plate 7 also includes a releasable coupling 9 for a power supply conduit which, for the pump of FIG. 1, is a pressure medium conveying conduit, not shown. The terminal plate is rotatable at least through 90°.

A flat, torus shaped bellows 11 confines a pump volume 10. The bellows is made of elastic material and positioned between two oppositely driven pressure plates 12 and 13, as shown in FIG. 1. The pressure plates are secured to dished power application members 23' and 24' having central cylinder chambers 23 and 24 as will be described in more detail below.

Figure 5:
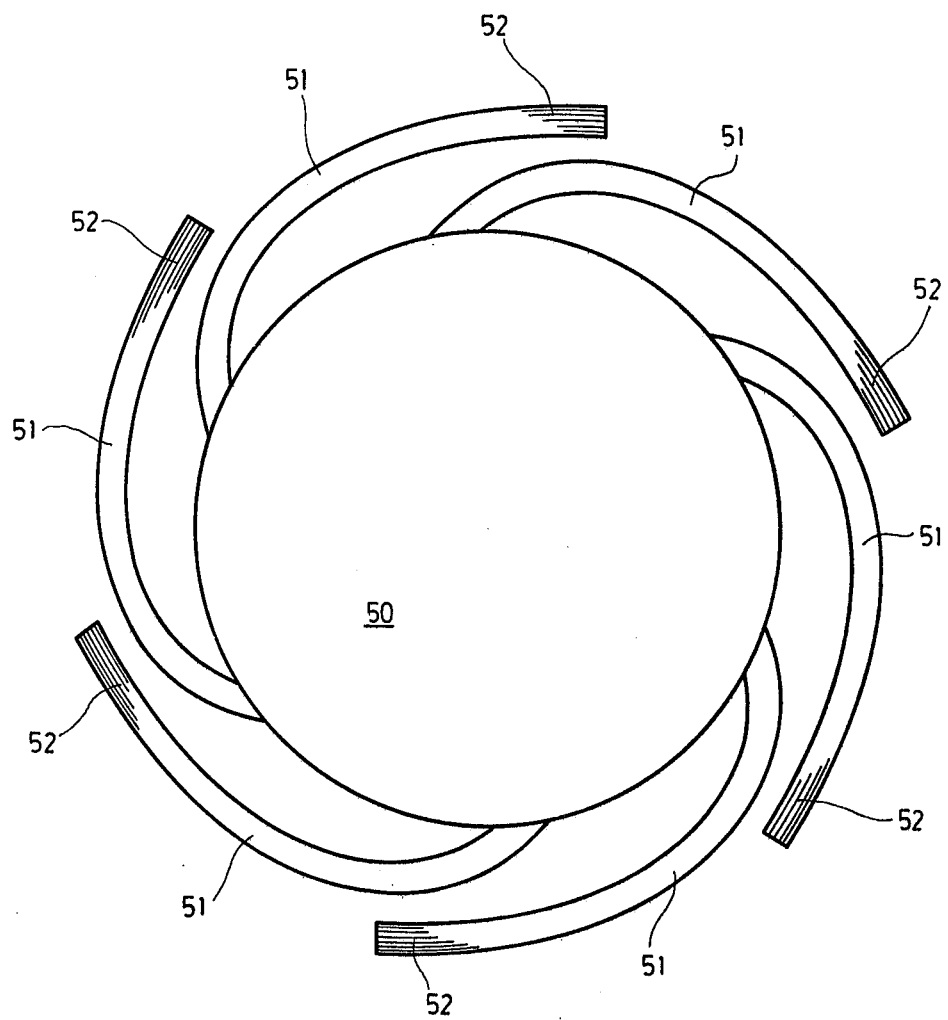
FIG. 5 is a top plan view of one type of a pressure plate with tangentially extending leaf spring means.

Two inlet and outlet pipe or hose conectors, of which only the connector 14 is shown in FIG. 1, are formed to extend in a tangential direction out of the bellows 11. Said connectors penetrate the pump housing 2 in the elastic, equatorial region 4 and are tightly attached to the housing 2 at the point of penetration by an adhesive bond or, as shown, by means of a fastening screw 16 and a retaining nut 17. The pressure plates 12 and 13 are constructed to have a built-in spring action. For example, the pressure plates may be made of elastically deformable material providing a spring loading by radially or tangentially extending fingers as shown in FIGS. 3 and 5.

The present pump is easily implanted into and placed in the body of a living being, due to the flexibility of the entire pump in its equatorial region, and due to its flat configuration as well as due to the rotatability of the connector terminal 7. Further, the connection to a power supply also contributes to a relatively easy implantation and placement.

Figure 3:
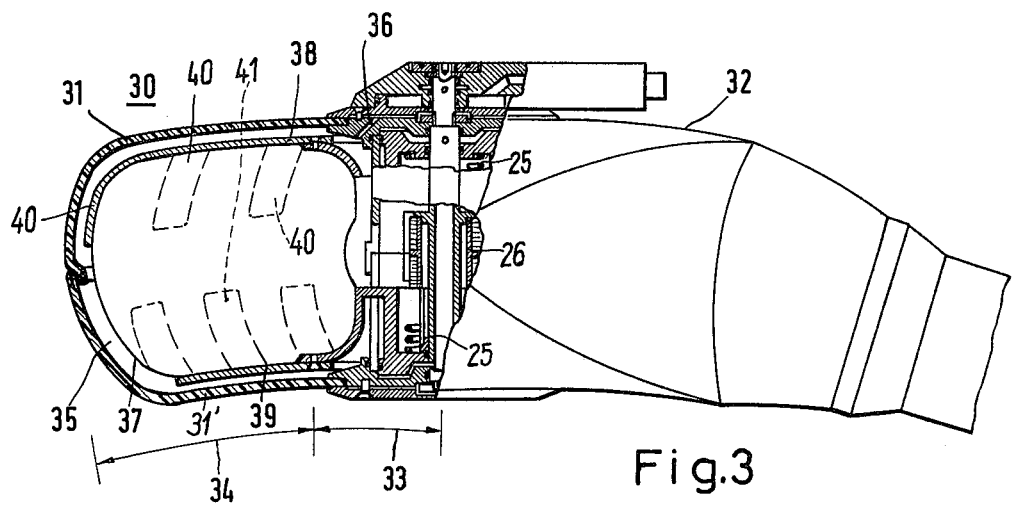
FIG. 3 is a side view, partially in section, of a further embodiment according to the invention, of a pump for an artificial heart.

By using a relatively thin walled, torus shaped bellows 11, which requires only a small amount of work or energy for its deformation, it is possible to construct the pressure plates 12 and 13 so that they provide a spring action, for example by means of elastic fingers, which encircle the bellows 11 in the equatorial region, whereby the fingers, such as shown at 40, 41 in FIG. 3, of one plate reach into spaces between the fingers in the other plate and vice versa, when the bellows 11 is compressed.

According to FIG. 1, the rotatable connector terminal 7 comprises a releasable coupling or connector 9, for a conduit conveying a pressure medium, as for example, a gas or liquid of a body compatible type, to drive the pressure plates 12 and 13 in opposite directions. The pressure medium acts in the pressure chambers 18 and 19, which are interconnected by pressure equalizing conduit means 20 and which are sealed by means of elastic membranes 21 and 22, respectively. The membranes 21 and 22 are stretched over the closed end of said cylinder chambers 23, 24 which are rigidly connected to the respective pressure plates 12, 13 by the members 23' and 24' respectively whereby the elastic pressure plates 12 and 13 are moved toward each other and against the force of a restoring spring 25 mounted in said cylinder chambers 23, 24 as shown in FIG. 1. Thus, a pump operation substantially free of vibrations is achieved and irregular pressure changes or shocks are suppressed while the pump delivers a smoothly pulsating pump action.

For an exact control of the pump and for an adaptation to varying pump power output requirements, and electromechanical displacement transducer 26 of known construction, for example an inductive displacement transducer 26, is located in the space 27 surrounded by said torus shaped bellows 11, as shown in FIG. 1. The signal conductors of the transducer 26 are connected to a connector plug 8 arranged on said connector terminal plate 7. The control means are not illustrated, since they are not part of the invention.

Figure 4:
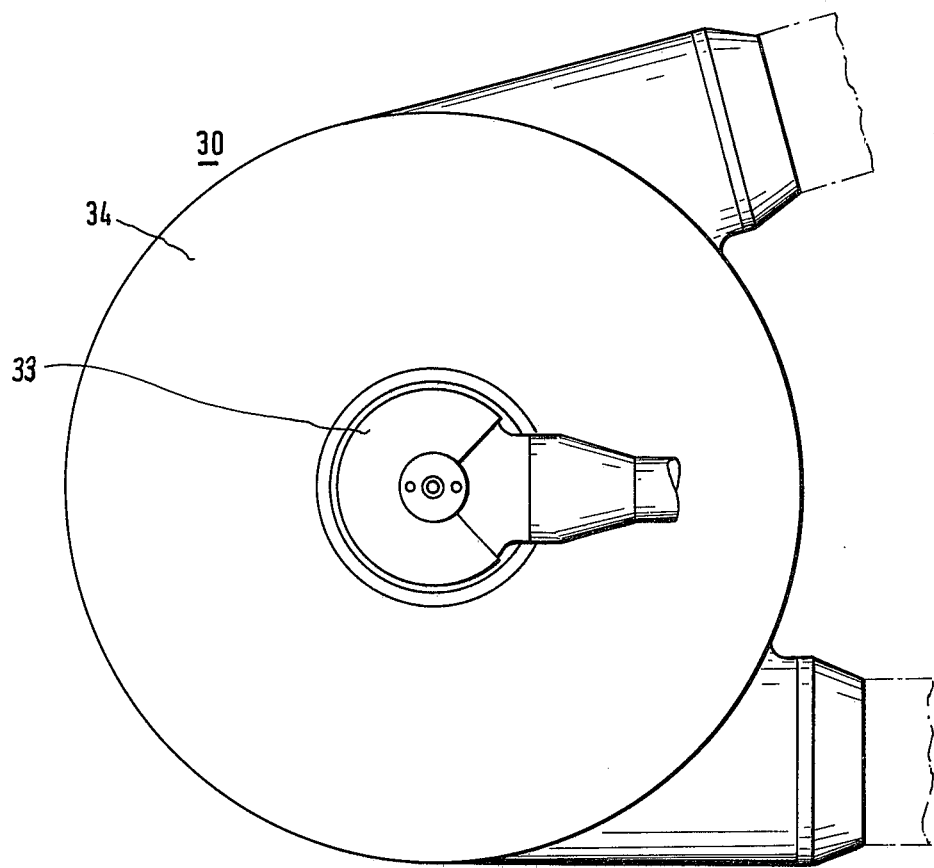
FIG. 4 is a top plan view of the pump in FIG. 3.

FIGS. 3 and 4 show as another embodiment a pump 30 for an artificial heart. The pump 30 is especially suitable to be driven by a pressure gas. The pump 1 of FIGS. 1 and 2 may be driven by liquid pressure, as well as by gaseous pressure media. However, the basic structure is the same in both embodiments. Hence, the above description also applies generally to FIGS. 3 and 4.

The pump housing 32 of the pump 30 comprises a surface 31 in its elastic equatorial region 34. The surface 31 has a callote or a hemispherical shape corresponding to the curvature of a diaphragm. Preferably, the opposite surface 31' also has an appropriate convex curvature whereby the pump achieves a good fit relative to the given form of an organism.

There is substantial conformity in the construction and configuration of the polar regions 3 in FIGS. 1 and 2 and 33 in FIGS. 3 and 4, whereby the pump 1 or 30 may be easily adapted to different shape and dimensional requirements at relatively low alteration costs.

According to FIG. 3, when a pressure gas is the driving means, it is possible to admit pressure to an area 35 lying between the torus shaped bellows 37 and the elastic part of the pump housing 32 through the pressure equalizing conduits 36. This air cushion protects the surrounding organs and the pump itself from severe loads due to movements of the user. Good sealing means are needed in the embodiment of FIGS. 1 and 2 while only relatively simple sealing means are needed in the embodiment of FIGS. 3 and 4. To increase the elasticity of the pump and to reduce the masses of moving weights, the torus shaped bellows 37 of the pump 30 is constructed with relatively thin walls. Referring to FIG. 3, the torus shaped bellows 37 is encircled by the elongated finger like leaf springs 40 and 41 forming part of the pressure plates 38 and 39, in the equatorial region. The springs 40 and 41 are so spaced that the springs of one pressure plate fit into the spaces between the springs of the other pressure plate. The pressure plates 13 and 12 of FIG. 1 may be similarly constructed, if desired. FIG. 5 shows a modification of a pressure plate 50 with spring fingers 51 extending substantially tangentially whereby the outer free ends 52 of the spring fingers 51 are shaped to conform to the shape of the bellows 37. The FIG. 3 embodiment also has a restoring spring 25 and transducer 26. Both configurations of the pump 1 or 30 are suitable for permanent insertion as an artificial heart as well as for time limited insertion required in a by-pass operation. The diagrams for the pressure and current flows correspond very well to the respective diagrams of a natural heart.

Although the invention has been described with reference to specific example embodiments, it is to be understood that it is intended to cover all modifications and equivalents within the scope of the appended claims.

What is claimed is:

1. A pump for an artificial heart pump, said pump housing having polar regions and an equatorial region, said polar regions comprising central housing means made of substantially rigid material, said equatorial region comprising a peripheral housing member made of flexible material, said central housing means and said peripheral housing member confining a hollow space, said pump housing further comprising inlet and outlet port means operatively secured to said peripheral housing member to extend tangentially relative to said equatorial region, connector means, and means rotatably securing said connector means to said central housing means on at least one side of said pump housing.

2. The pump housing of claim 1, wherein said connector means are rotatable at least through an angle of 90°.

3. The pump housing of claim 1, wherein said connector means are adapted for connection to power supply means.

4. The pump housing of claim 1, wherein said connector means are adapted for connection to pump control means.

5. The pump housing of claim 1, wherein said hollow space comprises substantially the shape of a rotational ellipsoid.

6. A pump for an artificial heart, comprising a pump housing having polar regions and an equatorial region, said polar regions comprising central housing means made of substantially rigid material, said equatorial region comprising a peripheral housing member made of flexible material, said peripheral housing member confining a variable volume hollow space, said housing further comprising inlet and outlet port means operatively secured to said peripheral housing member to extend tangentially relative to said equatorial region, connector means, means rotatably securing said connector means to said central housing means on at least one side of said pump, and power application means operatively communicating with said connector means for varying said variable volume hollow space.

7. The pump of claim 6, wherein said power application means comprise a relatively flat, torus shaped bellows of elastic material located in said hollow space, said bellows providing said variable volume, and pressure applying means operatively secured to said connector means and arranged for applying variable pressure to said bellows, said inlet and outlet port means being operatively secured to said bellows to extend tangentially relative to said bellows and through said housing member of flexible material, said pump further comprising means for securing said inlet and outlet port means in a sealing manner to said housing member of flexible material.

8. The pump of claim 7, wherein said pressure applying means comprise two pressure plates, one arranged on each side of said bellows, pressure chamber means, pressure transmitting means arranged to respond to pressure changes in said pressure chamber means to transmit such pressure changes to said pressure plates to move said pressure plates simultaneously in opposite directions, and elastic bias means operatively connected to said pressure transmitting means for returning said pressure plates into a starting position.

9. The pump of claim 8, wherein said pressure plates comprise spring action means cooperating with said bellows.

10. The pump of claim 9, wherein said spring action means comprise circumferentially spaced finger means extending radially outwardly, said finger means also being bent somewhat inwardly, said pressure plates being arranged in such a manner relative to each other that the finger means of one plate may reach into the spaces between the finger means of the other plate when the two plates move toward each other.

11. The pump of claim 9, wherein said spring action means comprise spaced finger means which extend substantially in a tangential direction.

12. The pump of claim 6, wherein said connector means comprise a rotatable connector plate including a conduit connector for a pressure supply, said power application means comprising a relatively flat, torus shaped bellows of elastic material located in said hollow space, pressure chamber means in said housing communicating with said conduit connector, elastic membrane means in said pressure chamber means, pressure transmitting means operatively associated with said membrane means and with said bellows whereby said pressure transmitting means may be driven in opposite directions in a pulsating manner in response to a respectively pulsating admission of a pressure medium into said pressure chamber means, and spring bias means operatively associated with said pressure transmitting means for repeatedly returning said pressure transmitting means into a starting position.

13. The pump of claim 12, wherein said pressure transmitting means comprise spring elastic means.

14. The pump of claim 6, further comprising transducer means located centrally in said housing means and responsive to volume variations in said housing, signal conduit means, and plug-in terminal means as part of said connector means, said signal conduit means leading from said transducer means to said plug-in terminal means.

15. The pump of claim 6, wherein said peripheral region of said housing made of flexible material comprises at least one section having a callote shaped surface configuration corresponding substantially to the curvature of a diaphragm.

16. The pump of claim 6, further comprising a bellows means in said hollow space, said bellows means providing said variable volume, a pressure space located substantially between said bellows means and said housing member of flexible material, pressure communicating means operatively connecting said pressure space to said connector means and thus to said power application means, and spring elastic bias means operatively connected to said bellows means for returning the latter to an expanded position in response to a diminishing pressure applied by said power application means.

* * * * *

UNITED STATES PATENT OFFICE
CERTIFICATE OF CORRECTION

Patent No. 4,091,471　　　　　　　　　　Dated May 30, 1978

Inventor(s) Christian Richter

It is certified that error appears in the above-identified patent and that said Letters Patent are hereby corrected as shown below:

Claim 1, line 1, after "pump" (first occurrence) insert --housing--.

Signed and Sealed this

Seventeenth Day of October 1978

[SEAL]

Attest:

RUTH C. MASON
Attesting Officer

DONALD W. BANNER
Commissioner of Patents and Trademarks